Aug. 14, 1962 G. J. VON ABRAMS Plant Pat. 2,162
ROSE PLANT
Filed Aug. 3, 1961
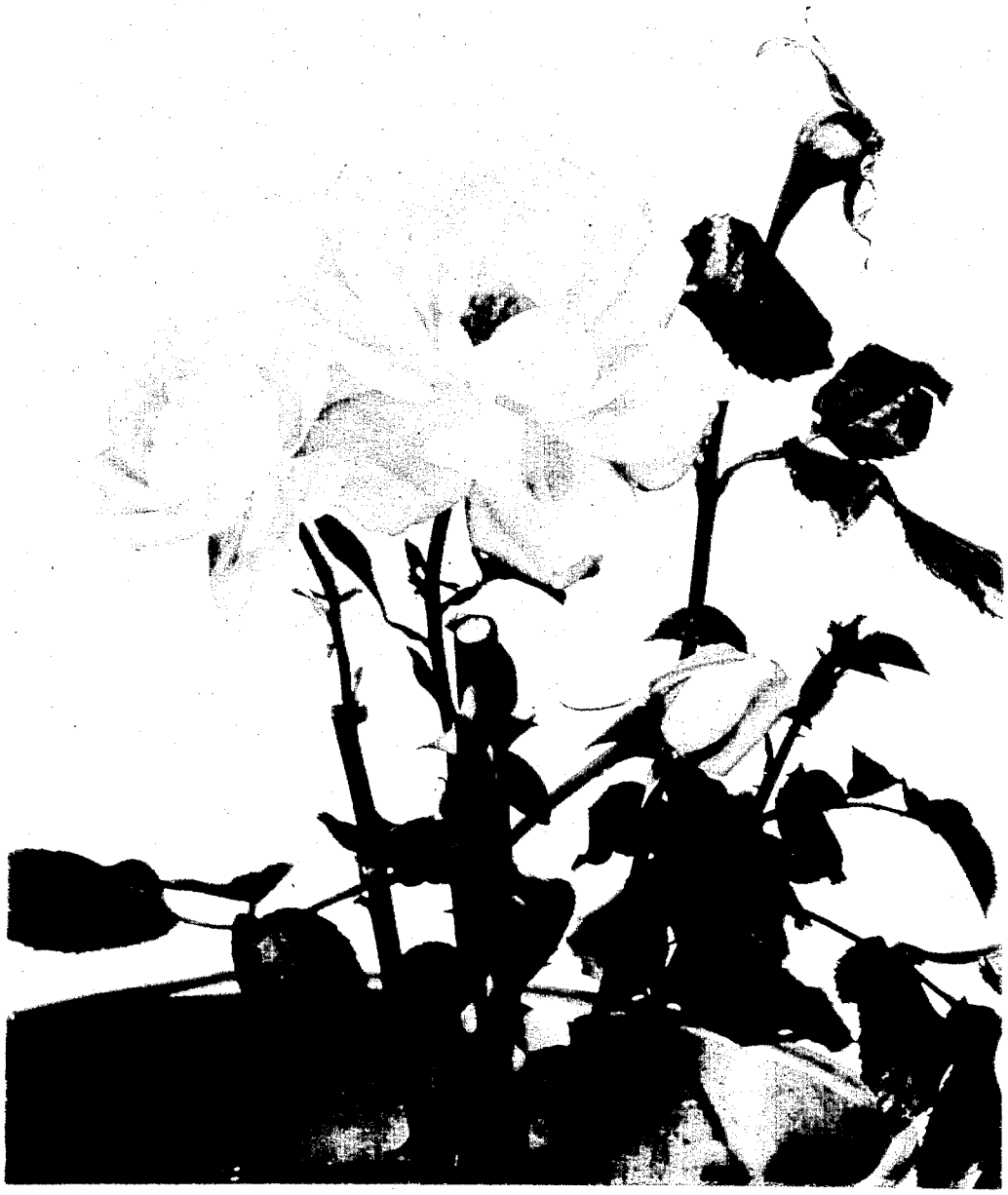
INVENTOR.
GORDON J. VON ABRAMS
BY F. R. Geiler,
ATTORNEY United States Patent Office Plant Pat. 2,162
Patented Aug. 14, 1962

2,162
ROSE PLANT

Gordon J. Von Abrams, Portland, Oreg., assignor to Eldon Pinkeney Dering, Scappoose, Oreg.

Filed Aug. 3, 1961, Ser. No. 129,193
1 Claim. (Cl. 47—61)

This invention comprises a new and distinct variety of rose plant of the commercial "hybrid tea" class which was obtained by crossing two hybrid rose plants (not in commerce) each of which had been obtained by crossing the rose variety "Multnomah" (Plant Patent No. 883) and the rose variety "Peace" (Plant Patent No. 591).

The objectives in the breeding of this new rose variety were, in part, the obtaining of a rose variety of exceptional vigor bearing large flowers the petals of which are red on one side and bright yellow on the other side, and also having bright glossy foliage. These objectives were achieved.

The principal distinguishing features of this new rose variety are the following: the plant is very tall and well formed, having heavy, but not awkward, branches; the flowers are large and the flower petals are yellow on the outside and red on the inside. Also the flowers are further characterized by a tendency to "quarter" during periods of rapid growth. The plant is semi-hardy and provides a tall, upright bush very suitable for outdoors both for garden decoration and for cut flowers.

The crossing of the varieties for producing this new variety took place at Scappoose, Oregon, in the spring of 1952. The first flower was produced from this new plant in the spring of 1954. Subsequent propagation of the plant has been by successive asexual reproductions through budgrafting at Scappoose, Oregon. The plant has retained its distinguishing characteristics throughout such propagation.

This new variety is somewhat similar, particularly in flower coloration, to the rose variety "Love Song" (Plant Patent No. 1,360). However, the plant of the new variety is taller and more vigorous than "Love Song," the foliage is slightly less glossy and the young growth is more red than "Love Song"; it has fewer petals, has more red on the outside of the bud, has a paler yellow on the outside of the mature petal, and bears more of its blooms on long single stems than "Love Song." Also the peduncle of the new variety is straight, whereas that of "Love Song" tends to be crooked.

The accompanying illustration shows the rose plant in color with separated blooms in different stages of development.

A description in detail of the new variety follows and in the description the following color references are used:

(1) Wilson, R. F.—Royal Horticultural Society Colour Chart, England 1940 (abbreviated "W.").

(2) Ridgway, R.—Color Standards and Color Nomenclature, Washington, D.C., 1912 (abbreviated "R.").

*Flowers*

The flowers are usually three to five per stem, on long strong stems; but sometimes are borne singly. The plant produces a moderate quantity of blooms outdoors and blooms continuously throughout the season. The flower longevity is greater than average.

Open flower:

*Size.*—Large (to six inches).

*Petalage.*—Double, ca. 40 petals.

*Form.*—High-centered. Petals at first lightly cupped later rolling outward at apical-lateral margins. Tends to "quarter" under conditions of cool weather and rapid growth.

*Fragrance.*—Light to moderate.

Petals:

*Substance.*—Medium thick, soft, flexible.

*Texture.*—Outside shiny; inside satiny.

*Shape and size (in open flower).*—Outside petal—large, obovate (i.e.—4.5 x 6.5 cm.); apex entire or irregular. Intermediate petal—obovate (i.e.—4 x 6 cm.); apex entire or irregular. Inside petals—usually contorted.

The following description of a newly-opened flower was made in August 1960 from specimens grown outdoors near Scappoose, Oregon.

*Color.*—Outside petal: Outer surface—spot of Aureolin (W. 3, p. 3) at basal tip. Base near Canary Yellow (W. 2/2, p. 2) fading gradually upward to near Canary Yellow (W. 2/3, p. 2) blending in the apical third to near Crimson (W. 22/2 to 22/3, p. 22). Inner surface—base near Canary Yellow (W. 2 to 2/2, p. 2) merging sharply with near Crimson (W. 22/1 to 22/2, p. 22) at a point ca. ⅓ to ¼ the distance from base to apex. Inside petal: Outer surface—base near Aureolin (W. 3, p. 3), fading gradually upward to near Saffron Yellow (W. 7/3, p. 7) often slightly flushed or marked with near Geranium Lake (W. 20/2, p. 20) near apex or along apical-lateral margins. Inner surface—base near Aureolin (W. 3, p. 3), changing abruptly to near Cherry (W. 722, p. 157) at a point about ⅓ or less the distance from base to apex.

*General color effect.*—Near Crimson (W. 22 to 22/1, p. 22).

The following description of a mature flower was made in August 1960, from specimens which had been open for a period of three days on a plant grown outdoors, near Scappoose, Oregon.

*Colors.* — Outside petal: Outer surface — base near Aureolin (W. 3/1, p. 3) fading gradually upward to Aureolin (W. 3/3, p. 3) or nearer white. The apical portion is very faintly flushed pale pink, paler than Rhodamine Pink (W. 527/3, p. 138). Inner surface—base near Aureolin (W. 3, p. 3) fading shortly upward to 3/1 or 3/2. At a point approximately ⅙ or less than ⅙ the distance from base to apex, the yellow area merges abruptly with near Tyrian Rose (W. 24 to 24/1, p. 24). Somewhat bluer near the apex (i.e.—near Solferino Purple, W. 26/2, p. 26). Inside petal: As outside petal, but less blue near the apex on the inner surface.

*General color effect.*—Near Rose Bengal (W. 25/1 to 25/2, p. 25).

Behavior in senescence: Color of inner surface of petals becomes gradually more blue (i.e.—to near Magenta (W. 27/1 to 27/2, p. 27)). The yellow color of the outer surface fades to near-white. Petals drop cleanly.

Bud:

*Peduncle.*—Size—medium large (i.e.—0.4 x 8 cm.). Strength—stiff. Color—near Scheeles Green (W. 860/3, p. 175). Surface—few very fine whitish hairs; very few small glandular cilia.

*Sepals.* — Size — medium (i.e. — 0.8 x 2.5 cm.). Form—spear-shape. Point — medium-long; aristate, seldom foliaceous. Lateral margins—none to several bristle-like appendages; most with glandular cilia, some entire. Surface: outer—glossy; near-smooth to slightly pubescent; inner—tomentose. Color: outer—near Scheeles Green (W. 860, p. 175); inner—near Corydalis Green (R. 29'''. GG–Y., Plate XLI). Behavior—reflex.

*Before calyx breaks.*—Size—medium. Form—long pointed; with medium-bristly terminal point. Surface—moderately smooth, glossy; slightly glandular; with few whitish hairs. Color — near Scheeles Green (W. 860 to 860/1, p. 175).

*As calyx breaks.*—Exposed petal color near Ruby Red (W. 827/1, p. 171).

*As first petal opens.*—Size of bud—large (i.e.—2.5 x 4 cm. ). Form of bud—long pointed. Color: Outer surface—near Aureolin (W. 3 to 3/1, p. 3) at base, to near Saffron Yellow (W. 7/2, p. 7) toward apex, irregularly flushed or marked with near Crimson (W. 22 to 22/1, p. 22). Inner surface—near Aureolin (W. 3, p. 3) at base, merging abruptly with near Cherry (W. 722, p. 157) at a point about ⅕ or less the distance from base to apex.

*Opening habit.*—Opens well under most conditions. May be delayed by wet cold weather, and bloom then tends to "quarter."

*Plant*

Foliage:

*Leaves.*—Compound; 5 to 7 leaflets; abundant; large.

*Leaflets.*—Substance — thick; hard; flexible. — Texture—smooth; glossy. Size—large (i.e.—terminal leaflet 6.5 x 8.5 cm.). Shape — broad ovate. Apex acuminate. Base very slightly cordate. Margin irregularly serrate. Color: Mature — upper surface darker than Spinach Green (W. 0960, p. 187). Under surface near Asphodel Green (R. 29'''. GG–Y., Plate XLI). Young—upper surface near, but somewhat darker and more red than Calla Green (R. 25. YG–Y. *m*, Plate V) flushed near Ox-blood Red (R. 1, RED. *k*, Plate 1), particularly along margins and main veins. Under surface green heavily flushed Deep Hellebore Red (R. 71''. V–RR. *i*, Plate XXXVIII).

*Rachis.* — Caliber — heavy. Upper side — groove ordinary; ridges with several gland-tipped cilia. Under side—nearly smooth, few sharply-hooked small thorns.

*Stipules.*—Size—large. Points — medium long; usually turned out less than 45°; nearly straight. Margins—lightly serrate; glandular.

*Disease resistance.*—Slightly better than average, but freely susceptible to "rust."

Growth:

*Habit.*—Very tall, upright, full.

*Vigor.*—Very vigorous.

*Canes (in second year of growth).*—Caliber—heavy. Surface—rough, moderately corky. Thorns, numerous, medium large, grayish brown. General color—gray-green.

*Main stems (of current year's growth).* — Caliber — heavy. Surface — moderately smooth; glaucous. Thorns—several large to very large; hooked downward; color brown; base near oval (i.e. 4 x 15 mm.). Color—near Parrot Green (R. 31. Y–G. *k*, Plate VI).

*Branches (currently bearing senescent flowers.)* — Caliber—heavy. Surface — glaucous; otherwise smooth. Thorns — many large (i.e. — 13 mm. long); hooked downward; color yellowish tan; base narrow oval (i.e.—2 x 9 mm.). Color — near Light Elm Green (R. 27'. G–Y. *k*, Plate XVII) flushed unilaterally near Dark Indian Red (R. 3''. O–R. *m*, Plate XXVII).

*New shoots (in rapid growth).*—Surface — smooth, slightly glaucous. Thorns — numerous; long; hooked slightly downward; base narrow oval; color near Ox-blood Red (R. 1, RED. *k*, Plate 1). Color—near Hay's Maroon (R. 1'. RED. *m*, Plate XIII).

Low-temperature tolerance: Slightly above average for class.

*Reproductive Organ*

Stamens:

*Quantity.*—Numerous.

*Position.*—Normal; immediately within corolla, on outer edge of disc.

*Filaments.*—Length irregular, from ca. 5 to 15 mm. Color reddish. Most but not all with anthers; some bearing contorted petaloids.

*Anthers.*—Large (i.e.—1 x 3 mm.). Yellowish.

*Pollen.*—Plentiful. Viable.

Pistils:

*Quantity.*—Moderate.

*Styles.*—Length ca. 8 mm. above disc; free; moderately contorted.

*Stigmas.*—Small; grayish.

*Ovaries.*—Enclosed.

Receptacle and calyx-tube:

*Size.*—Medium (i.e.—12 mm. diameter x 10 mm. high).

*Shape.*—Ordinary (short with rounded base).

*Disc.*—Normal; yellowish.

*Surface.* — Slightly glaucous. Few white hairs. Very slightly glandular.

*Color.*—Near Scheeles Green (W. 860/2, p. 175).

Fruit aggregate ("seed-pod"):

*Quantity.*—Readily formed; moderate number.

*Size.*—Large (i.e.—2.5 x 2.5 cm.).

*Shape.*—Globular.

*Sepals.*—Persistent.

*Surface.*—Smooth, glossy.

*Wall.*—Thick, fleshy.

*Color at maturity.*—Variable, orange.

Seeds: Numerous; large; viable.

Having thus disclosed my invention, I claim:

A new and distinct variety of rose plant of the "hybrid tea" class, substantially as shown and described, characterized particularly by its tall vigorous growth habit and its large flowers, the petals of which are red on their inside face and yellow on their outside face.

No references cited.